United States Patent [19] [11] 4,076,882
Fenster et al. [45] Feb. 28, 1978

[54] SHARPS DISPOSAL PADS

[76] Inventors: Larry A. Fenster, 301 Birch Drive, Roslyn, N.Y. 11576; Leo Fenster, 20100 W. Country Club Drive, N. Miami Beach, Fla. 33180

[21] Appl. No.: 755,951

[22] Filed: Dec. 30, 1976

[51] Int. Cl.² .......................... B32B 7/02; B32B 3/26
[52] U.S. Cl. .................................... 428/215; 428/213; 428/314; 428/315; 206/365; 206/438
[58] Field of Search ................ 206/365, 438; 428/213, 428/214, 215, 314, 315, 354, 355

[56] References Cited
U.S. PATENT DOCUMENTS
3,500,129  3/1970  Jowitt .................................... 428/314

Primary Examiner—William J. Van Balen
Attorney, Agent, or Firm—Abner Sheffer

[57] ABSTRACT

A foldable sharps disposal pad having a layer of polyurethane on a layer of cardboard, part of the polyurethane foam having a pressure sensitive adhesive thereon. The latter is in the form of a polyester film having a tacky styrene-butadiene rubber adhesive layer on each side.

4 Claims, 3 Drawing Figures

SHARPS DISPOSAL PADS

This invention relates to sharps disposal pads for use in surgical operations.

Figure 1:
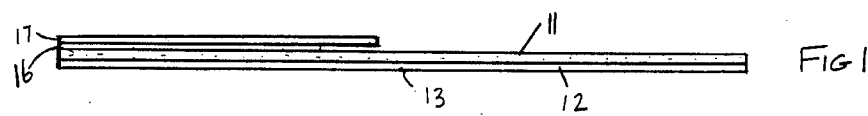
Figure 2:
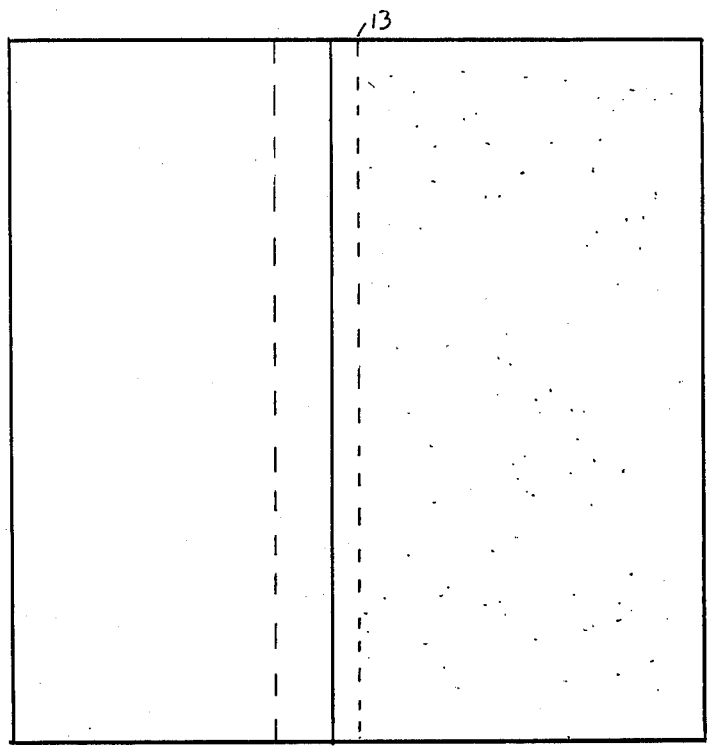
Figure 3:
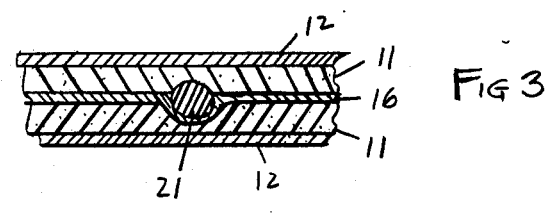

One embodiment of the invention is illustrated in the accompanying drawing in which FIG. 1 is a schematic side view of a sharps disposal pad, FIG. 2 is a plan view of the pad, and FIG. 3 is a schematic side view, considerably enlarged, in cross section showing a portion of the pad in folded condition, holding a sharp, such as a needle.

The sharps disposal pad comprises a thin layer 11 of elastomeric polyurethane foam adhesively bonded to a sheet 12 of cardboard. The cardboard has a median score line 13 along which the pad can be folded. On one portion of the foam layer 11 there is a layer 16 of supported pressure sensitive adhesive which (until use) is covered by a layer of lightly adhering release paper 17. The release paper completely covers the adhesive and extends past it over a portion of the foam which is free of adhesive, so that an adhesive-free edge of the paper can be grasped to peel the release paper off the adhesive. The whole structure is sterilized by radiation (e.g. radioactive cobalt radiation).

The pad may be of any appropriate size and shape, such as a 4 inch by 6 inch rectangle.

In use during a surgical operation the release paper is peeled off and the pad is employed with its foam face up. All disposable sharps (such as surgical needles) are placed on the foam; they may be placed on the tacky adhesive which retains them in position and/or they may be pushed into the foam to be held frictionally thereby. After (and during) the operation the sharps on the pad are counted to see that their number (and character) corresponds to the number employed during the operation, thus giving an indication as to whether any have been left in the patient. The pad carrying the sharps is then folded along the score line to bring the tacky adhesive into contact with the adhesive-free portion of the foam, thus closing the pad like a book. The contact retains the pad in a closed position with only the outside smooth coated face of the cardboard being exposed (except, of course along the edges). As seen in FIG. 3 the foam, being resilient, conforms to shape of the sharps, such as needle 21. The cardboard resists penetration by the sharps and keeps them enclosed within the folded structure.

The polyurethane foam layer is preferably of clickable (easily die-cut) foam which generally contains a water-repelling silicone. An example is #6200 Tenneco polyester polyurethane foam weighing about 1.75 – 2 lbs/cubic foot, having a cell count of 32 – 36 per linear inch (and a crisp cell count of 26 – 30). It is rather thin, such as about 0.06 to 0.1 inch (preferably about 0.08 inch) thick.

The cardboard layer is preferably solid bleached virgin sulfite board carrying a shiny coating on its outside. It is relatively non-porous, typically being of the type known in the trade as "medium density." Preferably it is about 20 mils thick.

In the past, the tacky adhesive layer has been a polyacrylate adhesive having an internal fibrous tissue support, and the foam has been bonded to the cardboard by a conventional dextrin adhesive.

It has now been found that much superior results in terms of longer shelf life (e.g. more enduring tackiness) are obtained when, in place of the fiber-reinforced polyacrylate adhesive layer, there is employed a thin non-fibrous substantially impermeable plastic film coated on both sides with a tacky pressure-sensitive rubber base adhesive, preferably having "SBR" (styrene-butadiene rubber) base. Particularly suitable is a film of polyester (such as polyethylene terephthalate) less than 1 mil thick (e.g. about ½ mil in thickness) having a layer of pressure sensitive SBR adhesive on each face. Both these pressure sensitive adhesive layers may be thicker than the film carrying them; for instance they may each be about 1 mil (e.g. 1.1 mil) thick. One preferred adhesive has an adhesion of about 70–80 ounces per inch. A typical film of polyester has an elongation at break of about 50–70% such as about 60%. The adhesive-coated film adheres very tightly to the polyurethane foam and when the pad is closed firmly it is practically impossible to open it without destroying the integrity of the foam.

It has now also been found that superior and more consistent adhesion of the foam to the cardboard is obtained by employing as the adhesive for this purpose a polyvinyl acetate aqueous emulsion of relatively high solids content such as 30% solids or more (e.g. 30–40% such as about 35%) and of viscosity above about 5000 centipoises such as about 6,000 to 10,000 centipoises. This works much better on the relatively impenetrable solid bleached sulfite cardboard. The polyvinyl acetate emulsion is applied to the cardboard as a layer, or spaced stripes, which may be for instance about 2 to 5 mils thick, the polyurethane foam layer is laid onto the wet emulsion on the cardboard and the emulsion is allowed to dry. The amount of polyvinyl acetate applied is such as to hold the foam mechanically to the cardboard. Thus in the final product one can peel the foam layer from the cardboard and polyvinylacetate without damaging the foam, leaving a rough deposit of polyvinyl acetate (which has been molded to the cellular conformation of the foam in contact therewith) but the bond is strong enough to resist any tendency for peeling of foam from cardboard when, in use, the release paper is peeled sharply from the foam.

The foregoing description is given by way of illustration; variations may be made therein without departing from the spirit of the invention.

We claim:

1. In a foldable sharps disposal pad comprising a layer of elastomeric polyurethane foam on a layer of cardboard, said polyurethane carrying a pressure sensitive adhesive layer covered by a release sheet, the improvement wherein said pressure sensitive adhesive layer comprises a substantially impermeable polymer film carrying a pressure sensitive rubber base adhesive on both sides of the film.

2. A pad as in claim 1 in which said adhesive is a styrene-butadiene rubber base adhesive and said film is a polyester film.

3. A pad as in claim 2 in which said film is a polyethylene terephthalate film.

4. A pad as in claim 3 in which said cardboard layer is bleached sulfite pulp cardboard and is bonded to said foam layer by dried polyvinyl acetate emulsion, said cardboard being about 0.02 inch thick, said foam layer being about 0.08 inch thick, said film being about ½ mil thick and said pressure sensitive adhesive being about 1 mil thick on each side of said film.

* * * * *